United States Patent [19]

Rosenthal et al.

[11] Patent Number: 4,585,656

[45] Date of Patent: Apr. 29, 1986

[54] TREATMENT OF HERPES

[76] Inventors: Harold R. Rosenthal; Laura Bert, both of 4 Laurel Pl., Eastchester, N.Y. 10709

[21] Appl. No.: 642,149

[22] Filed: Aug. 20, 1984

[51] Int. Cl.$^4$ .............................................. A61K 35/78
[52] U.S. Cl. ................................................. 424/195.1
[58] Field of Search ............................. 424/195, 195.1

[56] References Cited

U.S. PATENT DOCUMENTS 4,117,120  9/1985  Elderbaum ........................ 424/195

Primary Examiner—Jerome D. Goldberg
Assistant Examiner—John W. Rollins, Jr.
Attorney, Agent, or Firm—Thorpe, North & Western

[57] ABSTRACT

Herpes simplex, herpes varicella, and herpes zoster are treated by topical application of a composition comprising an effective amount of aloe vera and kelp. The composition can additionally contain an effective amount of jojoba oil.

8 Claims, No Drawings

TREATMENT OF HERPES

BACKGROUND OF THE INVENTION

The invention relates to medical treatment of herpes simplex infections, including herpes simplex, herpes varicella, and herpes zoster, as well as abscesses of the mouth, by topical application of a medicant composition.

Herpes simplex is an infection by herpes simplex virus which is marked by the eruption of one or more groups of vesicles or sores on the human body, especially on the vermillion border of the lips, at the external nares, on the glands, prepuce, or vulva. The infection is commonly recrudescent and reappears during other febrile illnesses or even physiological states such as menstruation and high stress. The infection has also been called, according to its site, fever blisters, cold sores, herpes facialis, herpes febrilis, herpes genitalis, herpes liabialis, and herpes progenitalis.

Herpes simplex virus Type 1 is usually located above the umbilicus and Type 2 is usually located below the umbilicus in the genital area. The two types are morphologically exact and can only be differentiated by means of serological techniques.

Herpes varicella, commonly known as chickenpox, and herpes zoster, commonly known as shingles, are infections which are also closely related to herpes simplex. In all the infections, the first occurence of sores from infectious herpes is preceded by symptoms including burning sensations, itching, fever, numbness, headaches, muscle aches, and swollen glands. An acute reaction to the initial outbreak may be so severe as to incapacitate the victim and eruptions may extend from a few days to several weeks or longer, in the case of herpes simplex.

Genital herpes is particularly severe in the case of pregnant women. During birth, the newborn baby is exposed to infection, blindness, brain damage, and the mortality rate for such newborn babies approaches three out of four.

As mentioned above, herpes simplex commonly reoccurs in most patients periodically throughout their lives. Subsequent recurrence of the lesions are signalled by the same symptoms as the original outbreak, in generally the same area where the previous vesicles occurred. Almost anything can cause a recurrence of an attack, such as emotional stress, poor diet, exposure to wind or sun, friction from tight clothing and insufficient sleep or rest.

Various treatments of herpes simplex have been proposed. U.S. Pat. No. 4,147,803 discloses the topical application of lauric diethanolamide to the area affected. Application of a mixture of boric acid, tannic acid, and salicylic acid is taught in U.S. Pat. No. 4,285,934. The use of lignosulfonate as a topical treating agent is disclosed in U.S. Pat. No. 4,185,097, and the application of kelp to the affected area is proposed in U.S. Pat. No. 4,117,120.

Objective: The principal objective of the present invention is to provide a new method of treating herpes simplex, herpes varicella (chickenpox) and herpes zoster (shingles) by topical administration of a medication which has good activity against the various herpes viruses and which further acts very quickly to effect essentially total relief of pain from the affected area. This and other objects and advantages of the invention will become apparent from the following description.

SUMMARY OF THE INVENTION

A composition for the topical treatment of herpes virus lesions comprises effective amounts of at least about 10% kelp and 20% aloe vera. In a preferred embodiment, the composition contains up to about 5% jojoba oil. All percentages given throughout the specification and claims are by weight.

DESCRIPTION OF THE INVENTION

It has been found that herpes virus infections can be effectively combatted by topical application to the affected area of an effective amount of a composition comprising as active ingredients aloe vera and kelp. In a preferred embodiment of the invention, the active ingredients include jojoba oil in addition to the aloe vera and kelp. The active ingredients are preferrably contained in a pharmaceutically inert carrier comprising various organic solvents, and aqueous-based or organic solvent-based emulsions. In addition to the active ingredients and inert carrier, the composition of the present invention may contain counter-reaction agents, odor controllers, and thickeners such as molasses, honey and lecithin. The composition of the present invention may also include stabilizers such as methyl paraben, propyl paraben or mixtures thereof.

Effective concentrations of each active ingredient in the composition of this invention, on a weight basis, are from about 10% to 20% kelp, preferably from about 12% to 15%, and from about 20% to 40% aloe vera, preferably from about 22% to 36%. When jojoba oil is incorporated into the composition as a preferred third active ingredient, it is employed in a concentration of from about 3% to 5%. The balance of the composition is substantially a pharmaceutically inert carrier comprising an organic solvent, a mixture of organic solvents, or an aqueous-based or organic solvent-based emulsion. The composition can, of course, contain stabilizers, counter-reaction agents, odor controllers and thickeners as mentioned previously.

As used throughout this specification and claims, the term "aloe vera" is meant to include the extract from the several species of the plant of the genus Aloes. Generally, the aloe vera extract contains about 96% water by weight. The term "kelp" is meant to include machine dried, powdered kelp. The term "jojoba oil" is meant to include the extract or oil obtained from the seeds and fruit of the evergreen shrub, simmondsia Californica.

The treatment of the herpes virus infection or other painful skin condition in accordance with this invention comprises topical application of the composition disclosed herein to the affected area on the person suffering from the infection. An effective amount of the composition is applied to the affected area 1 to 2 times a day until healing is effected. Generally, complete healing, i.e., disappearance of symptoms including lesions, will be achieved within about 1 to 2 days. The total relief of pain from the affected area will be achieved within several minutes, generally from about 3 to 10 minutes, depending upon the median size of the lesions when treatment is started.

The composition in accordance with the present invention is effective in the treatment of areas on the human body affected with herpes simplex virus, cold sores, lesions, warts (berrucae vulgaris) and blisters. The composition has also been found to be effective in treatment of external ulcers, and other painful skin conditions, bringing very quick relief from the pain experienced by such conditions, as well as an aid in healing of the condition.

The particular combination of ingredients of the invention appears to have a synergistic effect in healing herpes virus lesions compared to compositions containing the active ingredients alone. The relative effectiveness is indicated in the following table which illustrates the effects of treating a plurality of patients with compositions containing the individual ingredients and the synergistically active combination of active ingredients. The first composition consisted of, by weight, 25% aloe vera, 14% dried, powdered kelp and the balance being an inert carrier. The second composition consisted of, by weight 25% aloe vera, 14% dried, powdered kelp, 5% jojoba oil and the balance being an inert carrier. The third composition consisted of 100% aloe vera. The fourth composition contained 25% dried, powdererd kelp and the balance being an inert carrier. The fifth composition contained 100% jojoba oil. Each of these compositions was used to treat a number of respective individuals suffering from herpes virus lesions, and as mentioned above, the relative effectiveness of the respective compositions is shown in the following table:

| Composition No. | % of Patients Improved Within 2 to 3 Days |
| --- | --- |
| 1 | 95% |
| 2 | 100% |
| 3 | 10% |
| 4 | 60% |
| 5 | 5% |

The compositions of the present invention are easily and readily prepared by measuring proper quantities of the active ingredients and adding them singly or together to the pharmaceutically inert carrier. The carrier may be any liquid or creams which do not appreciably react with the active ingredients to reduce their efficacy, and which do not irritate the skin. As mentioned previously, various organic solvents, and aqueous-based or organic solvent-based emulsions can be used as the carrier. Additional components such as skin softeners may be added to the compositions of the active ingredients as long as the effectiveness of the resulting composition is not impaired. The invention is further illustrated with reference to the following Examples.

EXAMPLE 1

A woman had been suffering from an infection with herpes zoster for twelve years. She was in almost constant pain, with swelling about the abdomen. Surgery had been recommended to interrupt nerve tracts to the affected area. A composition similar to the second composition noted hereinbefore containing 25% aloe vera, 14% dried, powdered kelp, and 4% jojoba oil in a pharmaceutically inert carrier was applied to the affected area. The treatment process was repeated on a daily basis for several days after the first application. The woman was relieved of pain within 12 hours and relieved of itching within 24 hours. All discomfort had disappeared within three weeks. Five months following the treatment, the woman experienced a recurrence of itching and pain. The recurrence was abated by further application of the above composition to the affected area.

EXAMPLE 2

A male was afflicted with painful watery blisters on his hands. The composition as mentioned in Example 1 was applied to the blisters only once. The pain was relieved almost immediately, and the blisters disappeared overnight. There had been no recurrence in seventeen months following the initial treatment.

EXAMPLE 3

A young female college student who has been afflicted regularly with herpes simplex type one blisters since she was about three years old was treated by applying the composition as mentioned in Example 1 to a blister on her lip. The application was made in the afternoon of one day, and the blister was gone by the morning of the next day.

EXAMPLE 4

Three children of the same family, two males ages 6 and 3½, and a 14 month-old female, had herpes varicella (chickenpox). The two younger children had red spots starting to develop for about 12 hours when a composition as mentioned in Example 1 was applied to the red spots. The six-year-old child had developed the symptoms one to two days previously, and the composition was applied to the affected areas of the six-year-old child at the same time as the treatment of the two younger children. Itching stopped almost immediately in all three children, and the formation of blisters ceased in about 24 hours and disappeared in another 24 hours. Treatment was continued 2 to 3 times a day for 2½ days. The blisters went into remission without turning white or yellow, as in the normal progression of chickenpox. A fourth child about 10 years old, who had developed the symptoms earlier and had completed about six days of blisters before the outbreak of chickenpox in the other three children, still had red spots lingering. Application of the composition to the red spots made the redness disappear within hours.

EXAMPLE 5

A woman 70 years old was afflicted with herpes simplex lesions and blotches covering her face. A composition as mentioned in Example 1 was applied to her face, and she was relieved of pain within 40 minutes thereafter. The treatment was repeated daily for several days. The sores and blotches were reduced by about 80% within 36 hours and healed within 21 days.

EXAMPLE 6

A male 51 years old who had a 20-year history of herpes simplex type two had a new outbreak of four or five red spots on the left side of his penis near the head on the foreskin. The red spots were accompanied by pain and itching. A composition as mentioned in Example 1 was applied to the area of the red spots, and within eight hours, the red spots disappeared. The following day, additional red spots appeared on the right side of the penis. The man was unable to apply the composition of this invention immediately, and the spots developed into full blisters; however, within nine hours, after application, the vesicles were dry and healing, with the red spots fading. The man found one blister on the third day that had been missed the previous day on the right side of his penis. The composition of this invention was applied to this blister at 7:00 a.m. and the pain and itching ceased almost immediately. By 9:00 p.m. of that day, the last vesicle was dry, and the red spot was fading. In the past, this man had experienced outbreaks with pain and itching which lasted for four to five days before the sores went away. Approximately five months later a recurrence was treated, resulting in the initial spots and blisters disappearing within seven hours.

Although no intent is hereby expressed as to be limited in any way to any proposed mechanism by which the composition of the present invention operates, it is believed that active ingredients in the composition prevent the penetration of the herpes virus into other host cells. Untreated, the virus penetrates a host cell and replicates within the host cell until the host cell bursts (or lyses), causing the cell to die. The composition of this invention is believed to prevent penetration of the virus into other host cells by binding, blocking and/or inhibiting the viral enzyme, even when the virus is deep-seated. The composition contains negatively charged sulfated polyanions which are believed to bind themselves to the positively charged molecules on the surface of the virion and sterically inhibit adsorption of the virus by the cell. The external envelope of herpes virion contains a polyamine spermidine, which is positively charged, and it is believed that the negatively charged sulfated polyanions may be bound to the spermidine, thus inactivating the virus.

Although preferred embodiments of the invention have been disclosed, it is to be understood that various changes and modifications can be made without departing from the subject matter coming within the scope of the following claims, which subject matter is regarded as the invention.

We claim:

1. A method of treating herpes simplex, herpes varicella, and herpes zoster by topically applying to the affected area on the human body an effective amount of a composition comprising an effective amount of at least 20% aloe vera by weight and an effective amount of 10% dried, powdered kelp by weight.

2. A method as claimed in claim 1, wherein the composition comprises from about 20% to 40% aloe vera by weight, and from about 10% to 20% kelp by weight contained in an inert carrier.

3. A method as claimed in claim 1 wherein the composition further contains an effective amount of up to 5% of jojoba oil by weight.

4. A method as claimed in claim 3, wherein the composition comprises from about 20% to 40% aloe vera by weight, from about 10% to 20% kelp by weight, and from about 3% to 5% jojoba oil by weight contained in an inert carrier.

5. A composition for topical application to areas on the human body affected with herpes simplex, herpes varicella, and herpes zoster, said composition containing an effective amount of at least 20% aloe vera by weight and an effective amount of at least 10% dry, powdered kelp by weight.

6. A composition as claimed in claim 5 comprising from about 20% to 40% aloe vera by weight, and from about 10% to 20% kelp by weight contained in an inert carrier.

7. A composition as claimed in claim 5 which further contains an effective amount of up to 5% of jojoba oil by weight.

8. A composition as claimed in claim 7 comprising from about 20% to 40% aloe vera by weight, from about 10% to 20% kelp by weight, and from 3% to 5% jojoba oil by weight contained in an inert carrier.

* * * * *